United States Patent
Yokoo Yamazoe et al.

(10) Patent No.: US 11,919,833 B2
(45) Date of Patent: Mar. 5, 2024

(54) COMPOUND AND METHOD FOR PRODUCING SAME

(71) Applicant: MITSUBISHI GAS CHEMICAL COMPANY, INC., Chiyoda-ku (JP)

(72) Inventors: Aoi Yokoo Yamazoe, Chiyoda-ku (JP); Yutaka Kanbara, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 18/252,821

(22) PCT Filed: Apr. 12, 2022

(86) PCT No.: PCT/JP2022/017570
§ 371 (c)(1),
(2) Date: May 12, 2023

(87) PCT Pub. No.: WO2022/230656
PCT Pub. Date: Nov. 3, 2022

(65) Prior Publication Data
US 2023/0416187 A1 Dec. 28, 2023

(30) Foreign Application Priority Data
Apr. 26, 2021 (JP) .................. 2021-073893

(51) Int. Cl.
C07C 211/27 (2006.01)
C07C 209/48 (2006.01)
C07C 253/30 (2006.01)
C07C 255/33 (2006.01)

(52) U.S. Cl.
CPC .......... *C07C 211/27* (2013.01); *C07C 209/48* (2013.01); *C07C 253/30* (2013.01); *C07C 255/33* (2013.01)

(58) Field of Classification Search
None
See application file for complete search history.

(56) References Cited

U.S. PATENT DOCUMENTS

| | | |
|---|---|---|
| 2003/0229102 A1 | 12/2003 | Knobelsdorf et al. |
| 2006/0199951 A1 | 9/2006 | Wang |
| 2012/0214785 A1 | 8/2012 | Roth et al. |

FOREIGN PATENT DOCUMENTS

| | | | |
|---|---|---|---|
| CN | 103342663 A | * 10/2013 | ........... C07C 253/20 |
| CN | 103342663 A | 10/2013 | |
| CN | 104744237 A | 7/2015 | |
| JP | 2004-503527 A | 2/2004 | |

OTHER PUBLICATIONS

Written Opinion dated Jun. 21, 2022 in PCT/JP2022/017570 (with English Translation).
International Search Report dated Jun. 21, 2022, in PCT/JP2022/017570, filed on Apr. 12, 2022, citing documents 1-2, 15-16, & 25-26 therein, 2 pages.
S. Brenner and B Alterovich, Tetrahedron, Polymethylations of Bis(cyanomethyl) Benzenes, vol. 32, pp. 487-491 (1976).
Mono-c-methylation of arylacetonitriles and methyl arylacetates by dimethyl carbonate: a general method for the synthesis of pure 2-arylpropionic acids. 2-phenylpropionic acid. Organic Syntheses. Coll. 1999. vol. 76. pp. 169-173. DOI: 10.15227/orgsyn.076.0169, 5 pages.
Shang. R. et al. Synthesis of α-Aryl Nitriles through Palladium-Catalyzed Decarboxylative Coupling of Cyanoacetate Salts with Aryl Halides and Triflates. Angewandte Chemie. International Edition. 2011. vol. 50. No. 19. pp. 4470-4474. DOI: 10.1002/anie.201006763 scheme 5. compound 4i, 5 pages.

* cited by examiner

*Primary Examiner* — Joseph R Kosack
(74) *Attorney, Agent, or Firm* — Oblon, McClelland, Maier & Neustadt, L.L.P.

(57) ABSTRACT

Provided is a method for producing a methyl-adduct compound, the method including methylating, in the presence of potassium carbonate and dimethyl carbonate, a dinitrile compound represented by Formula (1) below to obtain a methyl-adduct compound represented by Formula (2) below:

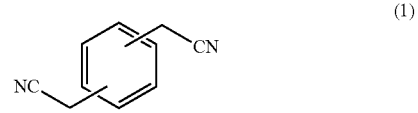

(1)

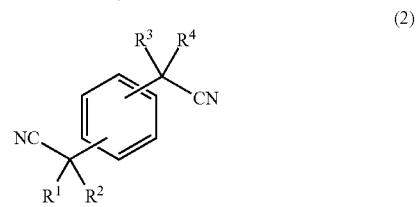

(2)

where in Formula (2), $R^1$~$R^4$ each independently represent hydrogen or methyl, and from one to three of $R^1$~$R^4$ are each methyl.

9 Claims, No Drawings

COMPOUND AND METHOD FOR PRODUCING SAME

CROSS-REFERENCE TO RELATED APPLICATIONS

The present application is a 35 U.S.C. § 371 national stage patent application of International patent application PCT/JP2022/017570, filed on Apr. 12, 2022, which is based on and claims the benefits of priority to Japanese Application No. 2021-073893, filed on Apr. 26, 2021. The entire contents of these applications are incorporated herein by reference.

TECHNICAL FIELD

The present invention relates to a compound and a method for producing the same.

BACKGROUND ART

A compound in which the benzyl position of para-bezenediethanamine is methylated is useful as a raw material for a resin such as a polyamide. As the method for producing the methyl-adduct compound, a method in which phenylenediacetonitrile is methylated and subsequently hydrogenated is known. For example, Patent Document 1 discloses that methyl iodide is used as a methylation agent, and a borane complex is used as a reducing agent. In addition, Non-Patent Literature 1 also discloses that methyl iodide is used as a methylation agent. Incidentally, Non-Patent Literature 2 discloses that if phenyl acetonitrile is used as the substrate, dimethyl carbonate is used as the methylation agent.

CITATION LIST

Patent Document

Patent Document 1: JP 2004-503527 T

Non-Patent Literature

NPL 1: Tetrahedron, Vol. 32, pp. 487-491 (1976)
NPL 2: Organic Syntheses, Coll. Vol. 10, p. 640 (2004), Vol. 76, p. 169 (1999)

SUMMARY OF INVENTION

Technical Problem

In Patent Document 1 and NPL 1, methyl iodide is used as the methylation agent, but methyl iodide is toxic to the human body. In addition, when methyl iodide is used, methyl groups are easily introduced in excess, and it is difficult to control the number of methyl groups (in other words, selective methylation is difficult). Therefore, the reaction must be carried out at a low temperature for a short amount of time and is not suited for industrial applications.

In Patent Document 1, the borane complex is used as a reduction catalyst, but borane complexes are expensive and difficult to reuse, and thus are not industrially suited.

Therefore, an object of the present invention is to provide a method for more selectively methylating phenylenediacetonitrile in comparison to a case in which methyl iodide is used as the methylation agent.

Solution to Problem

As a result of diligent research, the present inventors discovered that by using potassium carbonate and dimethyl carbonate in combination, phenylenediacetonitrile can be selectively methylated and an industrially-suited production method can be achieved, and thereby the inventors completed the present invention.

The present invention includes the following embodiments.

[1]

A method for producing a methyl-adduct compound, the method including methylating, in the presence of potassium carbonate and dimethyl carbonate, a dinitrile compound represented by Formula (1) below:

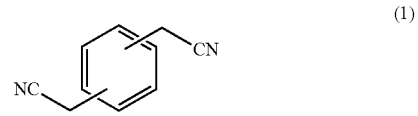

to obtain a methyl-adduct compound represented by Formula (2) below:

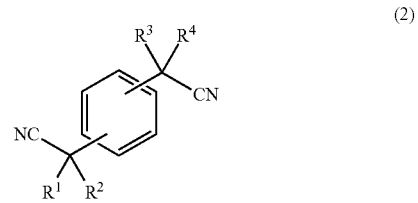

where in Formula (2),
$R^1 \sim R^4$ each represent independently hydrogen or methyl, and from one to three of $R^1 \sim R^4$ are each methyl.

[1-1]
The method according to [1], wherein two of $R^1 \sim R^4$ are methyl.

[1-2]
The method according to [1] or [1-1], wherein either $R^1$ or $R^2$, and either $R^3$ or $R^4$ are each methyl.

[2]
The method according to any one of [1] to [1-2], wherein Formula (1) is Formula (1A) below:

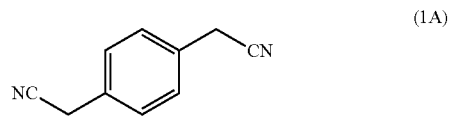 [SMILES: N#CCc1ccc(CC#N)cc1]

and Formula (2) is Formula (2A) below:

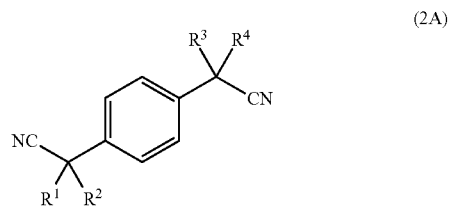

where in Formula (2A), $R^1 \sim R^4$ are as described above.

[3]
The method according to any one of [1] to [2], wherein a molar ratio of the potassium carbonate to the dinitrile compound is from 2.0 to 3.5.
[3-1]
The method according to any one of [1] to [3], wherein the molar ratio of the potassium carbonate to the dinitrile compound is from 2.0 to 3.0.
[3-2]
The method according to any one of [1] to [3-1], wherein the molar ratio of the potassium carbonate to the dinitrile compound is from 2.0 to 2.5.
[3-1A]
The method according to any one of [1] to [3-2], wherein a molar ratio of the dimethyl carbonate to the dinitrile compound is from 3.0 to 18.0.
[3-2A]
The method according to any one of [1] to [3-1A], wherein the molar ratio of the dimethyl carbonate to the dinitrile compound is from 5.0 to 14.0.
[3-3A]
The method according to any one of [1] to [3-2A], wherein the molar ratio of the dimethyl carbonate to the dinitrile compound is from 7.0 to 10.0.
[4]
The method according to any one of [1] to [3-3A], wherein the methylation is carried out at a temperature of from 180 to 230° C.
[4-1]
The method according to any one of [1] to [4], wherein the methylation is carried out at a temperature of from 190 to 220° C.
[4-2]
The method according to any one of [1] to [4-1], wherein the methylation is carried out at a temperature of from 200 to 210° C.
[5]
A method for producing a diamino compound, the method including hydrogenating a methyl-adduct compound produced by the method according to any one of [1] to [4-2] to obtain a diamino compound represented by Formula (3) below:

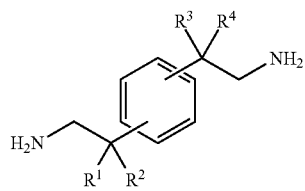

(3)

where in Formula (3), $R^1$~$R^4$ are as described above.
[6]
The method according to [5], wherein Formula (3) is Formula (3A) below:

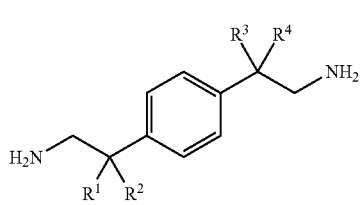

(3A)

where in Formula (3A), $R^1$~$R^4$ are as described above.
[7]
The method according to [5] or [6], wherein the hydrogenation is carried out in the presence of a solid hydrogenation catalyst.
[7-1]
The method according to any one of [5] to [7], wherein the hydrogenation is carried out in the presence of a Raney catalyst.
[7-2]
The method according to any one of [5] to [7-1], wherein the hydrogenation is carried out in the presence of Raney cobalt.
[8]
A compound selected from the group consisting of diamino compounds represented by Formulas (3-1) to (3-7) below:

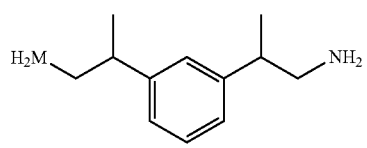

(3-1)

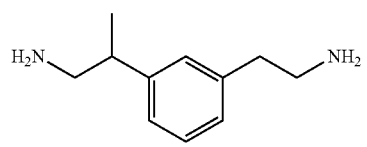

(3-2)

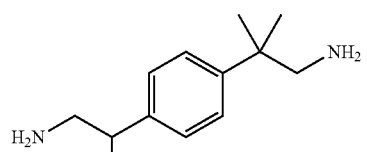

(3-3)

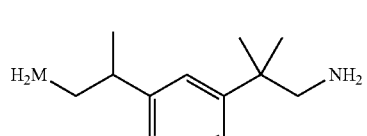

(3-4)

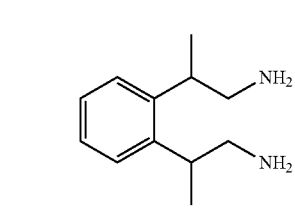

(3-5)

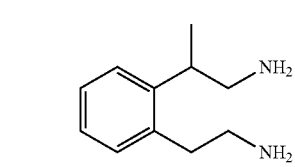

(3-6)

-continued

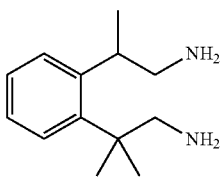
(3-7)

[9]
A compound selected from the group consisting of methyl-adduct compounds represented by Formulas (2-1) and (2-2) below:

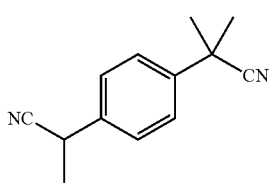
(2-1)

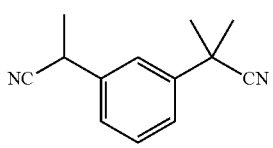
(2-2)

Advantageous Effects of Invention

According to the present invention, a method for selectively methylating phenylenediacetonitrile can be provided.

DESCRIPTION OF EMBODIMENTS

Hereinafter, embodiments of the present invention will be described in detail; however, the present invention is not limited to these embodiments, and various modifications may be made within a range that does not depart from the spirit of the invention.

Compound Production Method

Methylation Reaction

One embodiment of the present invention pertains to a method for producing a methyl-adduct compound by methylating, in the presence of potassium carbonate and dimethyl carbonate, a dinitrile compound represented by Formula (1) below to obtain a methyl-adduct compound represented by Formula (2) below:

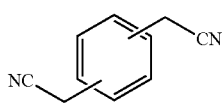
(1)

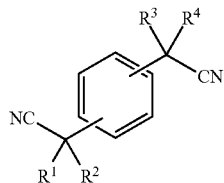
(2)

where in Formula (2), $R^1$~$R^4$ each independently represent hydrogen or methyl, and from one to three of $R^1$~$R^4$ are each methyl.

In the production method according to the present embodiment, a dinitrile compound represented by Formula (1) can be selectively methylated by using potassium carbonate and dimethyl carbonate in combination. Herein, "selectively methylated" means to control the number of methyl groups to be introduced.

From one to three of the $R^1$~$R^4$ are methyl, preferably two of the $R^1$~$R^4$ are methyl, and more preferably, either $R^1$ or $R^2$, and either $R^3$ or $R^4$ are methyl.

Although not particularly limited, Formula (1) and Formula (2) are preferably Formula (1A) below and Formula (2A) below, respectively:

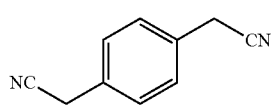
(1A)

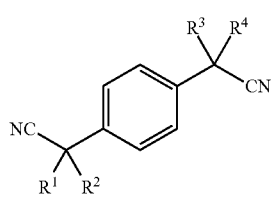
(2A)

where in Formula (2A), $R^1$~$R^4$ are as described above.

A molar ratio of the potassium carbonate to the dinitrile compound is preferably from 2.0 to 3.5, more preferably from 2.0 to 3.0, and even more preferably from 2.0 to 2.5. By setting the molar ratio to the range described above, a compound in which either $R^1$ or $R^2$, and either $R^3$ or $R^4$ are methyl can be selectively obtained.

The molar ratio of the dimethyl carbonate to the dinitrile compound is preferably from 3.0 to 18.0, more preferably from 5.0 to 14.0, even more preferably from 7.0 to 10.0. Setting the molar ratio to 3.0 or greater results in an accelerated reaction, and setting the molar ratio to 18.0 or less enables an increase in economic feasibility.

The reaction temperature of the methylation reaction is preferably from 180 to 230° C., more preferably from 190 to 220° C., and even more preferably from 200 to 210° C. By setting the reaction temperature to the range described above, a compound in which either $R^1$ or $R^2$, and either $R^3$ or $R^4$ are methyl can be selectively obtained.

The methylation reaction may be carried out until the reaction is completed, but the reaction time may be, for example, from 2 to 16 hours, from 4 to 12 hours, or from 6 to 8 hours.

Hydrogenation Reaction

The production method according to the present embodiment can further comprise hydrogenating the methyl-adduct compound obtained in the methylation reaction to obtain a diamino compound represented by Formula (3) below:

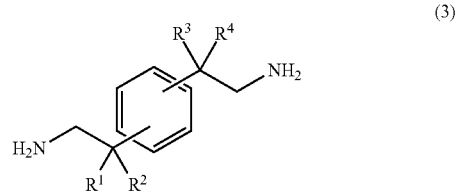
(3)

where in Formula (3), $R^1$–$R^4$ are as described above.

Although not particularly limited, Formula (3) is preferably Formula (3A) below:

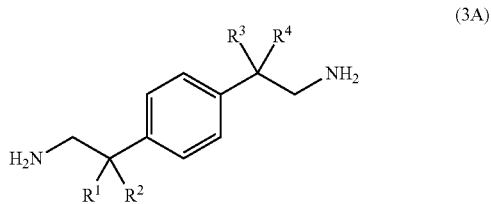
(3A)

where in Formula (3A), $R^1$–$R^4$ are as described above.

The hydrogenation reaction is preferably carried out under a hydrogen atmosphere in the presence of a hydrogenation catalyst. As the hydrogenation catalyst, a catalyst used in a normal nitrile hydrogenation reaction can be used, and specifically, a catalyst containing Ni and/or Co can be used. In general, a catalyst in which Ni and/or Co is supported by $Al_2O_3$, $SiO_2$, diatomaceous earth, $SiO_2$—$Al_2O_3$, or $ZrO_2$ through a precipitation method, or a Raney catalyst such as Raney nickel or Raney cobalt is suitably used. A solid catalyst can be used repeatedly, and thus is suitable for industrial production. Among these, from the perspective of more effectively and more reliably advancing the reaction, a Raney cobalt catalyst and a Raney nickel catalyst are preferable. One of these catalysts may be used alone, or two or more may be used in combination.

The mass ratio of the methyl-adduct compound to the hydrogenation catalyst is preferably from 2 to 30, more preferably from 5 to 20, and even more preferably from 8 to 10. When the mass ratio of the methyl-adduct compound to the hydrogenation catalyst is set to within the range described above, the yield and selectivity of the obtainable diamine compound can be increased.

A solvent used in a normal hydrogenation reaction can be used in the hydrogenation reaction, and specific examples includes liquid ammonia, ammonia water, alcohols such as methanol, ethanol, 1-propanol, 2-propanol, 1-butanol, 2-butanol, and tert-butanol, and aromatic hydrocarbons such as meta-xylene, mesitylene, and pseudocumene. One of these solvents may be used alone, or two or more may be used in combination.

The molar ratio of ammonia to the methyl-adduct compound is preferably from 10 to 150, more preferably from 25 to 100, and even more preferably from 40 to 50. When the molar ratio is set to greater than or equal to 10, there is a downward trend in generation of high boiling point compounds such as dimers and an upward trend in reaction performance, and when the molar ratio is set to 150 or less, the time required to remove liquid ammonia thereafter is reduced, and thus production efficiency is improved.

The reaction temperature of the hydrogenation reaction is preferably from 40 to 160° C., more preferably from 60 to 140° C., and even more preferably from 80 to 120° C. Setting the reaction temperature of the hydrogenation reaction to 40° C. or higher improves reactivity, and setting the reaction temperature of the hydrogenation reaction to 160° C. or lower tends to decrease high boiling point compounds such as dimers.

The pressure of the hydrogenation reaction is preferably from 1 to 20 MPa, more preferably from 4 to 16 MPa, and even more preferably from 8 to 12 MPa. When the pressure of the hydrogenation reaction is set to within the range described above, the yield and the selectivity of the obtainable diamine compound tends to increase.

The hydrogenation reaction may be carried out until the reaction is completed, but the reaction time may be, for example, from 0.5 to 8 hours, from 1 to 6 hours, or from 2 to 4 hours.

Compound

One embodiment of the present invention relates to a diamino compound represented by Formulas (3-1) to (3-7) below:

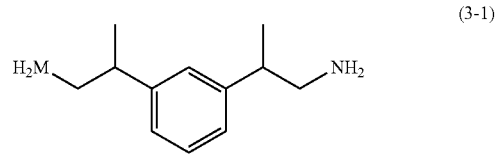
(3-1)

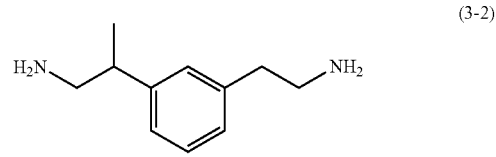
(3-2)

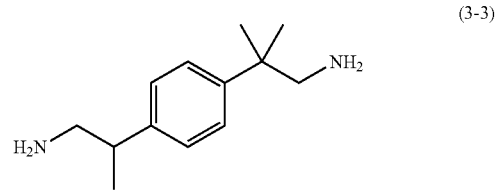
(3-3)

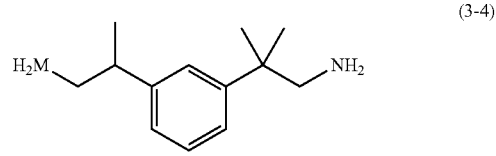
(3-4)

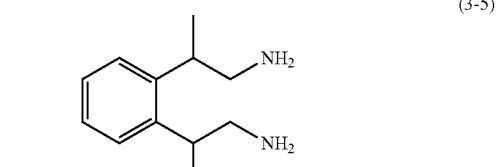
(3-5)

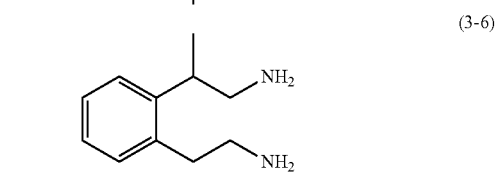
(3-6)

-continued (3-7)

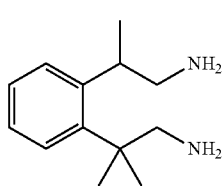

An embodiment of the present invention also relates to a methyl-adduct compound represented by Formulas (2-1) and (2-2) below:

(2-1)

(2-2)

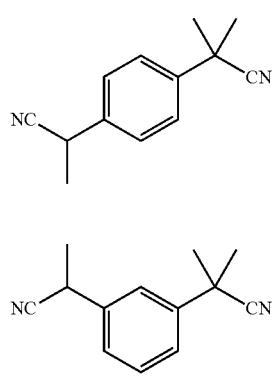

EXAMPLES

Hereinafter, the present invention will be described in further detail with reference to examples, but the technical scope of the present invention is not limited to these examples.

Example 1

Methylation

A 300 mL pressure-resistant reactor made of SUS316 was charged with 25.2 g of 1,4-phenylenediacetonitrile, 125 g of dimethyl carbonate, and 50.5 g of potassium carbonate as a base, the reactor was subjected to nitrogen replacement, the inside of the reactor was heated to 210° C., and a methylation reaction was allowed to proceed for 6.8 hours.

After the completion of the reaction, the reactor was cooled to room temperature, and the produced carbon dioxide was released. Next, 200 mL of water and 200 mL of a diethyl ether solvent were added, fractionation was implemented, the organic solvent layer was collected, and the solvent was removed by a rotary evaporator. The obtained crystals were analyzed by gas chromatography. The results indicated that the reaction yield of 2,2'-(1,4-phenylene) dipropanenitrile, which is a dimethyl adduct (dimethylated product), was 90.3%.

Details of the gas chromatography mentioned in the examples are as follows. Note that the reaction yields were all calculated by an area percentage of the components detected by gas chromatography.

Model: "GC 2010 PLUS", available from Shimadzu Corporation
Column: Product name "HP-1 ms", available from Agilent Technologies, Inc., 30 m length×0.25 mm inner diameter, 0.25 μm film thickness Conditions: Carrier gas, He (constant pressure: 73.9 kPa)
Injection port temperature: 300° C.
Detector: FID
Detector temperature: 300° C.
Column oven temperature: Started at 50° C., heated to 175° C. at 5° C./min, then heated to 320° C. at 20° C./min, and then held at 320° C. for 30 minutes.

2. Hydrogenation

A 300 mL pressure-resistant reactor made of SUS316 was charged with 29.0 g of the 2,2'-(1,4-phenylene)dipropanenitrile, synthesized as described above, 105 g of liquid ammonia as a solvent, and 2.99 g of Raney cobalt (available from W.R. Grace & Co.) as a catalyst, after which hydrogen gas was introduced into the reactor until the reaction pressure became 4 MPa. Next, the inside of the reactor was heated to a reaction temperature of 100° C., and when the predetermined temperature was reached, the contents of the reactor were stirred at 750 rpm with an electromagnetic stirring blade while hydrogen gas was continuously supplied into the reactor such that a reaction pressure of 10 MPa was uniformly maintained, and an amination reaction (nitrile hydrogenation reaction) through hydrogen addition was advanced for 180 minutes. After the completion of the reaction, the liquid ammonia was distilled off, and the reaction product was dissolved in methanol to remove the catalyst and then analyzed by gas chromatography. The results indicated that the reaction yield of 2,2'-(1,4-phenylene) bis(propan-1-amine), which is a dimethyl adduct (dimethylated product), was 92.5%. The reaction yield of a monomethylated product was 0.5%, and the reaction yield of a trimethylated product was 0.7%.

Example 2

A 300 mL pressure-resistant reactor made of SUS316 was charged with 5.0 g of 1,4-phenylenediacetonitrile, 56.1 g of dimethyl carbonate, and 18.9 g of potassium carbonate as a base, the reactor was subjected to nitrogen replacement, the inside of the reactor was heated to 205° C., and a methylation reaction was allowed to proceed for 6.7 hours.

After the completion of the reaction, the reactor was cooled to room temperature, and the produced carbon dioxide was released. Next, 200 mL of water and 200 mL of a diethyl ether solvent were added, fractionation was implemented, the organic solvent layer was collected, and the solvent was removed by a rotary evaporator. The obtained crystals were analyzed by gas chromatography. The results indicated that the reaction yield of 2,2'-(1,4-phenylene) dipropanenitrile, which is a dimethyl adduct (dimethylated product), was 70.0%.

Example 3

A 300 mL pressure-resistant reactor made of SUS316 was charged with 5.0 g of 1,4-phenylenediacetonitrile, 55.3 g of dimethyl carbonate, and 18.8 g of potassium carbonate as a base, the reactor was subjected to nitrogen replacement, the inside of the reactor was heated to 170° C., and a methylation reaction was allowed to proceed for 6.7 hours.

After the completion of the reaction, the reactor was cooled to room temperature, and the produced carbon dioxide was released. Next, 200 mL of water and 200 mL of a diethyl ether solvent were added, fractionation was implemented, the organic solvent layer was collected, and the solvent was removed by a rotary evaporator. The obtained crystals were analyzed by gas chromatography. The results indicated that the reaction yield of 2,2'-(1,4-phenylene)dipropanenitrile, which is a dimethyl adduct (dimethylated product), was 30.7%.

Example 4

A 300 mL pressure-resistant reactor made of SUS316 was charged with 5.0 g of 1,4-phenylenediacetonitrile, 54.8 g of dimethyl carbonate, and 18.7 g of potassium carbonate as a base, the reactor was subjected to nitrogen replacement, the inside of the reactor was heated to 245° C., and a methylation reaction was allowed to proceed for 6.7 hours.

After the completion of the reaction, the reactor was cooled to room temperature, and the produced carbon dioxide was released. Next, 200 mL of water and 200 mL of a diethyl ether solvent were added, fractionation was implemented, the organic solvent layer was collected, and the solvent was removed by a rotary evaporator. The obtained crystals were analyzed by gas chromatography. The results indicated that the reaction yield of 2,2'-(1,4-phenylene)dipropanenitrile, which is a dimethyl adduct (dimethylated product), was 1.3%.

The results of Examples 1 to 4 are shown in Table 1.

to obtain a methyl-adduct compound represented by Formula (2) below:

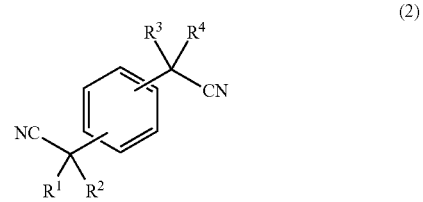

(2)

where in Formula (2), $R^1$~$R^4$ each independently represent hydrogen or methyl, and from one to three of $R^1$~$R^4$ are each methyl.

TABLE 1

| | | | Example 1 | Example 2 | Example 3 | Example 4 |
|---|---|---|---|---|---|---|
| Component | Substrate | mol | 0.16 | 0.03 | 0.03 | 0.03 |
| | $K_2CO_3$ | mol | 0.37 | 0.14 | 0.14 | 0.14 |
| | Dimethyl carbonate | mol | 1.39 | 0.62 | 0.61 | 0.61 |
| | $K_2CO_3$/substrate | molar ratio | 2.3 | 4.4 | 4.3 | 4.3 |
| | Dimethyl carbonate/substrate | molar ratio | 8.7 | 19.9 | 19.6 | 19.4 |
| Reaction Conditions | Reaction temperature | ° C. | 210 | 205 | 170 | 245 |
| | Reaction time | hours | 6.8 | 6.7 | 6.7 | 6.7 |
| GC Measurements | Conversion rate | GC area % | 100 | 100 | 83 | 100 |
| | mono-methyl adduct | GC area % | 0.5 | 0.1 | 46.5 | 0 |
| | di-methyl adduct | GC area % | 90.3 | 70 | 30.7 | 1.3 |
| | tri-methyl adduct | GC area % | 3.2 | 20.6 | 0.2 | 26.2 |
| | quad-methyl adduct | GC area % | 0.8 | 1.3 | 0 | 44.8 |

This patent application claims priority from the Japanese Patent Application No. 2021-073893 (filed on Apr. 26, 2021). All the contents of the Japanese patent application are incorporated herein by reference.

The invention claimed is:

1. A method for producing a methyl-adduct compound, the method comprising methylating, in the presence of potassium carbonate and dimethyl carbonate, a dinitrile compound represented by Formula (1) below:

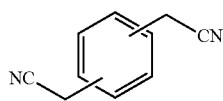

(1)

2. The method according to claim 1, wherein Formula (1) is Formula (1A) below:

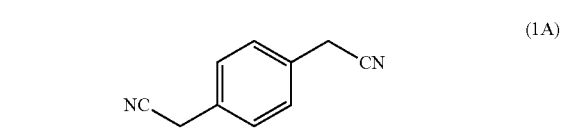 [SMILES: N#CCc1ccc(CC#N)cc1]

(1A)

and,
Formula (2) is Formula (2A) below:

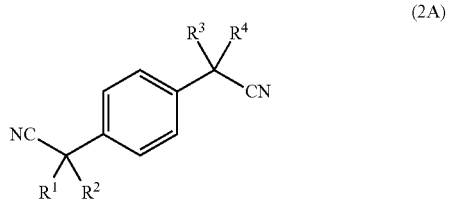

(2A)

where in Formula (2A), $R^1$~$R^4$ are as described above.

3. The method according to claim 1, wherein a molar ratio of the potassium carbonate to the dinitrile compound is from 2.0 to 2.5.

4. The method according to claim 1, wherein the methylation is carried out at a temperature of from 180 to 230° C.

5. A method for producing a diamino compound, the method comprising hydrogenating a methyl-adduct compound produced by the method according to claim 1 to obtain a diamino compound represented by Formula (3) below:

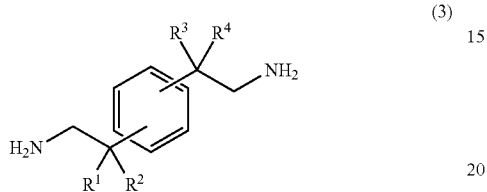
(3)

where in Formula (3), $R^1$~$R^4$ are as described above.

6. The method according to claim 5, wherein Formula (3) is Formula (3A) below:

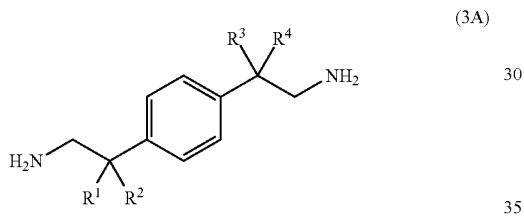
(3A)

where in Formula (3A), $R^1$~$R^4$ are as described above.

7. The method according to claim 5, wherein the hydrogenation is carried out in the presence of a solid hydrogenation catalyst.

8. A compound selected from the group consisting of diamino compounds represented by Formulas (3-1) to (3-7) below:

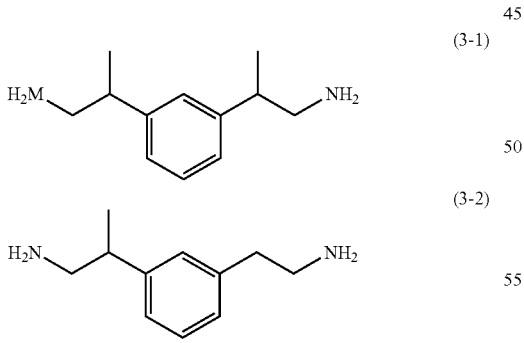
(3-1)

(3-2)

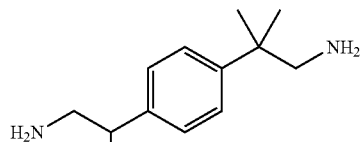
(3-3)

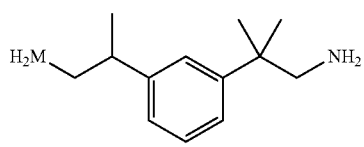
(3-4)

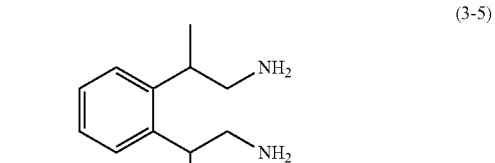
(3-5)

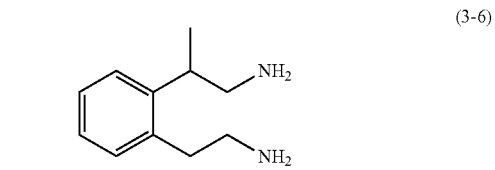
(3-6)

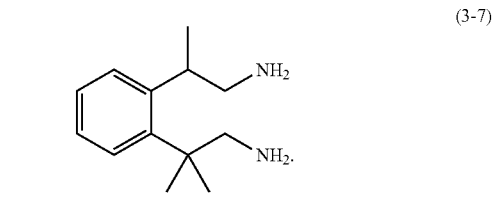
(3-7)

9. A compound selected from the group consisting of methyl-adduct compounds represented by Formulas (2-1) and (2-2) below:

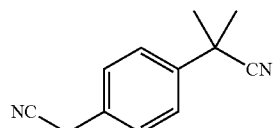
(2-1)

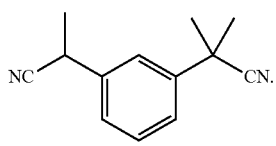
(2-2)

* * * * *